(12) United States Patent
Li et al.

(10) Patent No.: US 7,481,978 B2
(45) Date of Patent: Jan. 27, 2009

(54) APPARATUS FOR ASPIRATING LIQUIDS FROM SEALED CONTAINERS

(75) Inventors: William Weigong Li, Miami, FL (US); Craig R. Veiner, Miami, FL (US); Sergio Cabrera, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 664 days.

(21) Appl. No.: 11/088,157

(22) Filed: Mar. 23, 2005

(65) Prior Publication Data

US 2006/0216208 A1    Sep. 28, 2006

(51) Int. Cl.
*B01L 3/02* (2006.01)
*G01N 1/00* (2006.01)

(52) U.S. Cl. ............ 422/100; 422/63; 422/65; 73/863.85; 73/864.24; 73/864.74

(58) Field of Classification Search ............ 422/100, 422/63, 65; 73/863.85, 864.74, 864.24
See application file for complete search history.

(56) References Cited

U.S. PATENT DOCUMENTS

| | | | |
|---|---|---|---|
| 4,609,017 A | | 9/1986 | Coulter et al. |
| 4,927,545 A | * | 5/1990 | Roginski ............... 210/745 |
| 5,433,922 A | | 7/1995 | Parker et al. |
| 5,455,007 A | | 10/1995 | Calvo et al. |
| 5,483,843 A | * | 1/1996 | Miller et al. ............ 73/864.23 |
| 5,517,867 A | | 5/1996 | Ely et al. |
| 5,665,309 A | * | 9/1997 | Champseix et al. ........... 422/63 |
| 5,900,557 A | * | 5/1999 | Tanihata et al. .......... 73/863.01 |
| 5,935,523 A | | 8/1999 | McCandless et al. |
| 6,132,686 A | * | 10/2000 | Gallup et al. ............. 422/130 |
| 6,322,752 B1 | * | 11/2001 | Siddiqui et al. ............ 422/100 |
| 6,350,412 B1 | * | 2/2002 | Williams et al. ............. 422/65 |
| 6,360,794 B1 | * | 3/2002 | Turner ....................... 141/329 |
| 6,537,434 B1 | * | 3/2003 | McGrath et al. ............ 204/459 |
| 6,544,799 B1 | * | 4/2003 | Lewis et al. ................ 436/180 |
| 6,605,257 B1 | * | 8/2003 | Nakazawa et al. ............ 506/40 |
| 6,627,156 B1 | * | 9/2003 | Goodale et al. ............... 422/99 |
| 6,706,245 B2 | * | 3/2004 | Neal et al. .................. 422/100 |
| 6,752,965 B2 | * | 6/2004 | Levy ........................... 422/99 |
| 6,833,113 B2 | * | 12/2004 | Sentoh ....................... 422/100 |
| 6,866,820 B1 | * | 3/2005 | Otto et al. .................... 422/63 |
| 6,872,362 B2 | * | 3/2005 | Schmidt et al. ............ 422/104 |
| 7,134,459 B2 | * | 11/2006 | Carlson et al. .............. 141/130 |
| 7,205,158 B2 | * | 4/2007 | Pankratz et al. ............. 436/180 |
| 7,291,309 B2 | * | 11/2007 | Watson et al. ................. 422/63 |

(Continued)

*Primary Examiner*—Brian R. Gordon
(74) *Attorney, Agent, or Firm*—Warren W. Kurz; Mitchell E. Alter (57) ABSTRACT

Apparatus for aspirating liquid from a container, e.g., a test tube, having a puncturable stopper includes a pair of stepper motors that share a common linear actuator or drive member. One motor operates to axially advance the linear drive member (preferably a lead screw) to a position in which it serves to position a rigidly connected tube-detector/stripper member in engagement with the top of a stopper on a tube. Thereafter, the second motor operates to move along the surface of the same drive member to advance an aspiration probe through the engaged stopper and into a liquid aspirating position within the tube. Preferably, a linear guide rail, slidably-mounted on a frame that supports the liquid-aspirating apparatus, serves to guide both the movement of the aspiration probe and the linear drive member. As a result of the shared components, the apparatus is highly precise and reliable.

9 Claims, 8 Drawing Sheets

U.S. PATENT DOCUMENTS

2002/0015665 A1* 2/2002 Lindsey et al. ................ 422/64
2002/0025581 A1* 2/2002 Schmidt et al. ............. 436/180
2006/0088443 A1* 4/2006 Mattila et al. ................. 422/63
2006/0134793 A1* 6/2006 Key et al. ..................... 436/63

* cited by examiner

APPARATUS FOR ASPIRATING LIQUIDS FROM SEALED CONTAINERS

BACKGROUND OF THE INVENTION

1. Field of the Invention

The present invention relates to improvements in apparatus for aspirating liquids, such as biological specimens, from containers for processing. The invention is particularly useful in automated hematology instruments for extracting blood samples from sealed test tubes and the like for analysis.

2. The Prior Art

In conducting tests on biological liquids, it is common to employ automated instruments to extract liquid specimens from sealed containers, e.g., test tubes and the like. Such instruments typically include a movably-mounted sample aspiration probe that is adapted to puncture a rubber stopper atop a stationary specimen container to access and aspirate the liquid therein. These instruments often include a mechanism for sensing the presence of a specimen container at a desired specimen-aspiration position before the probe is moved in a direction to expose the probe tip, and most instruments include a device for stripping the rubber stopper from the aspirating probe as the probe is withdrawn from the container to prevent the stopper (and the container to which it is sealed) from following the movement of the probe due to frictional forces between the probe and stopper.

An automated instrument of the above type is disclosed in U.S. Pat. No. 5,517,867 to Ely et al. The disclosed apparatus is adapted to move a liquid-aspiration probe along a vertical axis into and out of a stoppered test tube containing a liquid of interest. The aspiration probe is supported in a vertical orientation above the test tube by a rigid, horizontally-extending arm that forms part of a frame. Such arm is raised and lowered by lead screw that is incrementally rotated by a motor. As the lead screw rotates in a first direction, the probe-supporting arm is lowered to a position in which the tip of the aspiration probe punctures a rubber stopper that seals the liquid to be aspirated within the tube. Further rotation of the lead screw in the same direction serves to position the probe tip in an aspiration position below the liquid level in the tube. Following liquid aspiration, the stepper motor operates to rotate the lead screw in the reverse direction, thereby raising the probe-supporting arm to a position in which the probe tip clears the top of the tube. To strip the rubber stopper from the aspiration probe during withdrawal of the probe from the tube, a downward force is applied to the stopper during upward movement of the probe. Such force is provided by a relatively massive second arm that extends horizontally, i.e., parallel to the probe-supporting first arm, and hangs downwardly from the first arm in a positioned intermediate the bottom of the first arm and the top of the test tube. The bottom surface of the second arm supports a "foot" that serves, during the downward movement of the first arm, to both guide the vertical travel of the aspiration probe, and to detect and position the underlying test tube so that the center of the rubber stopper is aligned with the path of the probe tip.

In liquid aspirating instruments of the above type wherein the tip of an aspiration probe is used to puncture a rubber stopper that seals the liquid in the container, the friction between the external surface of the probe and the rubber stopper can easily exceed 10-12 pounds. Considering that there can be additional frictional forces at work in guiding the downward movement of a weighted plate used to apply a stripping force to the tube stopper in instruments of the above-described type, the required weight of such plate may be as much as 18-20 pounds to assure that the stripper mechanism operates reliably. Thus, it will be appreciated that this approach is disadvantageous if only from the standpoint that it adds considerable weight to the instrument.

In U.S. Pat. No. 5,935,523 to McCandless, another automated apparatus is disclosed for accessing a liquid in a sealed container. This apparatus addresses the stripping problem noted above and provides several different solutions. First, to reduce the frictional force between the rubber seal on the container and a penetrating aspiration probe, an independent cap-piercing member is provided for cutting a slit in the cap (stopper) of a container (a test tube) before the aspiration probe enters the tube through the stopper. The slit, of course, facilitates movement of the probe through the stopper by reducing the frictional forces between the two. Further, means are provided for lubricating the cap-piercing member before it slices through the cap, and a residue of lubricant on the stopper will further reduce the stripping force required to separate the aspiration probe from the probe following aspiration. Finally, a "foot" which presses on the stopper during aspiration is mechanically locked in place by a solenoid-operated latch that operates during the liquid-aspiration and probe removal procedures. Thus, the use of a weighted foot, as taught by the above reference, is obviated through the combination of these relatively extreme features. While the aspirating apparatus of McCandless et al. does, indeed, facilitate the stripping function, it does so at the cost of a relatively complex mechanism. Further, the apparatus may be viewed as problematic in that it requires repositioning of the entire liquid aspiration apparatus after cap-piercing has been effected to align the aspiration probe with the container axis, and it further requires substantially perfect parallel alignment between two independently movable shafts, i.e., the aspiration probe and the cap-piercing member. The latter can be particularly problematic since any binding friction caused by the misalignment between the two shafts can produce a malfunction of the apparatus.

SUMMARY OF THE INVENTION

In view of the foregoing discussion, an object of this invention is to provide an improved apparatus for aspirating a liquid from a sealed container, such as a test tube or the like.

Compared to the prior art instruments discussed above, the liquid aspirating apparatus of the invention is improved from the standpoint that it is substantially simpler in construction, i.e., it requires fewer components, and it is relatively light in weight, requiring no relatively massive weight to steady the position of the liquid container while the aspiration probe is removed from a stopper that it has punctured to gain access to the liquid to be aspirated.

In accordance with a preferred embodiment of the invention, apparatus for aspirating a volume of liquid contained in a sealed tube having a puncturable stopper at one end of the tube comprises the combination of the following elements: (a) a support frame; (b) a first drive motor supported by the frame and adapted, in response to having a first electrical current applied thereto, to selectively and incrementally advance a linear drive member, preferably a lead screw or linear rack, along a predetermined path towards or away from the puncturable stopper on tube, such path being substantially parallel to the central longitudinal axis of the tube; (c) a tube detector/stripper member mounted at one end of the linear drive member, such tube detector/stripper member being adapted to engage the top of the puncturable stopper as the linear drive member is advanced along the predetermined path towards the puncturable stopper, whereby said tube detector/stripper member detects that a tube is in a position to have liquid aspirated therefrom; (d) a second drive motor supported by the linear drive member and being adapted, in response to having a second electrical current applied thereto, to selectively and incrementally move in along the axis of the linear drive member, towards or away from the puncturable stopper; and (e) an aspiration probe rigidly connected to the second drive motor, such aspiration probe being aligned with the central longitudinal axis of the tube and having a sharp distal tip adapted to puncture the puncturable stopper and thereby enter the interior of the tube as the second drive motor moves along the surface of the linear drive member towards the puncturable stopper. To strip the aspiration probe from the stopper after liquid aspiration, a holding current is applied to the first drive motor, thereby holding the linear drive member in a position in which the tube detector/stripper member exerts a holding force on the top of an underlying tube stopper during removal of the aspiration probe from the tube interior. Preferably, a linear guide rail is provided to guide the linear drive member along its predetermined path, such linear guide rail being slidably supported by the frame and rigidly connected to the second drive motor, whereby the linear guide rail moves with the linear drive member as the latter is driven along its predetermined path by the first drive motor. Also, it is preferred that the tube-detector/stripper member comprises a housing defining a probe-washing chamber in which the probe tip can be washed after each liquid aspiration.

By virtue of the invention, components that often serve independent functions in conventional liquid aspirating instruments are shared by different subsystems, thereby reducing component count and cost. For example, a linear drive member (which is most preferably a lead screw) is acted upon by the first drive motor to position the tube detector/stripper member in contact with a tube stopper. This same drive member further serves as a mechanism by which the second drive motor can be selectively and incrementally advanced towards and away from the sealed tube in order to position the tip of the aspiration probe in a position to aspirate liquid from the sealed tube, as well as to withdraw the probe from the tube. Similarly, a linear rail that serves to guide the linear drive member along its predetermined (preferably vertical) path so as to detect and properly position an underlying tube stopper, also serves to guide the aspiration probe towards engagement with the center of the tube stopper.

The invention and its advantages will be better understood from the ensuing detailed description of preferred embodiments, reference being made to the accompanying drawings in which like reference characters denote like parts.

DETAILED DECRIPTION OF PREFERRED EMBODIMENTS

Referring now to the drawings, FIGS. 1-4 illustrate a preferred apparatus 10 for selectively aspirating liquid contained in each of a plurality of sealed containers C supported in an upright orientation by a rack R. As illustrated, each container may be in the form of a conventional test tube or the like having a puncturable stopper S, e.g., made of a suitable rubber or synthetic rubber, that acts to seal the normally open end of the tube. While the tubes may vary in size considerably, as illustrated, the tube-support rack operates to arrange their respective longitudinal axes at equal distances and in a common vertical plane. From the description below, it will be appreciated that the liquid aspirating apparatus of the invention is capable of aspirating liquid from any of the various tube sizes that the rack can accommodate. Further, it will be understood that, during use of the liquid aspirating apparatus, the tube rack remains stationary while the liquid aspiration apparatus moves relative to each tube in order to extract liquid therefrom, one at a time. Prior to use of the apparatus 10, a rack-transport system associated with a liquid-analyzing instrument system (not shown) serves to transport individual racks of tubes and to precisely position each rack of containers in the same position in an X/Y plane for liquid aspiration. (Refer to the X/Y/Z coordinate system shown in FIG. 1.) Thus, the liquid aspiration apparatus of the invention need only support a liquid aspiration probe P for movement in an X/Z plane, which is the central vertical plane of the container rack.

Apparatus 10 includes a support frame 12 comprising a pair of spaced, parallel end brackets 14 and 15 interconnected by a pair of spaced, parallel rods 16 and 17. Preferably, each of the rods has a circular cross-section and, together, they provide a fixed support on which the aspiration probe and its support assembly 20 (described below) can slide horizontally, along the X-axis, as indicated by the arrow A in FIG. 1. Such movement enables the aspiration probe to be brought into vertical alignment with the central longitudinal axis A' of each tube in order to sequentially access the liquid contained in each of the tubes. The probe-support assembly 20 is mounted for movement along the X-axis on a truck 22 (best shown in FIG. 8) that is slidably-mounted on the cylindrical rods 16 and 17 via a pair of sleeve bearings 23 and 24 carried by the truck housing. The position of the truck along the X axis is controlled by a drive motor M1 mounted on end bracket 15. Preferably, motor M1 comprises a conventional stepper motor that operates to advance an endless drive belt 26 about a pair of spaced pulleys 28 (only one being shown) rotatably supported by the end brackets 14 and 15. The drive belt extends parallel to the X-axis, and truck 22 is rigidly connected to one reach of the belt by a clamp 29. Thus as the belt advances in either direction about its supporting pulleys, truck 22 follows along, moving laterally, from side-to-side, along the X axis.

Figure 2:
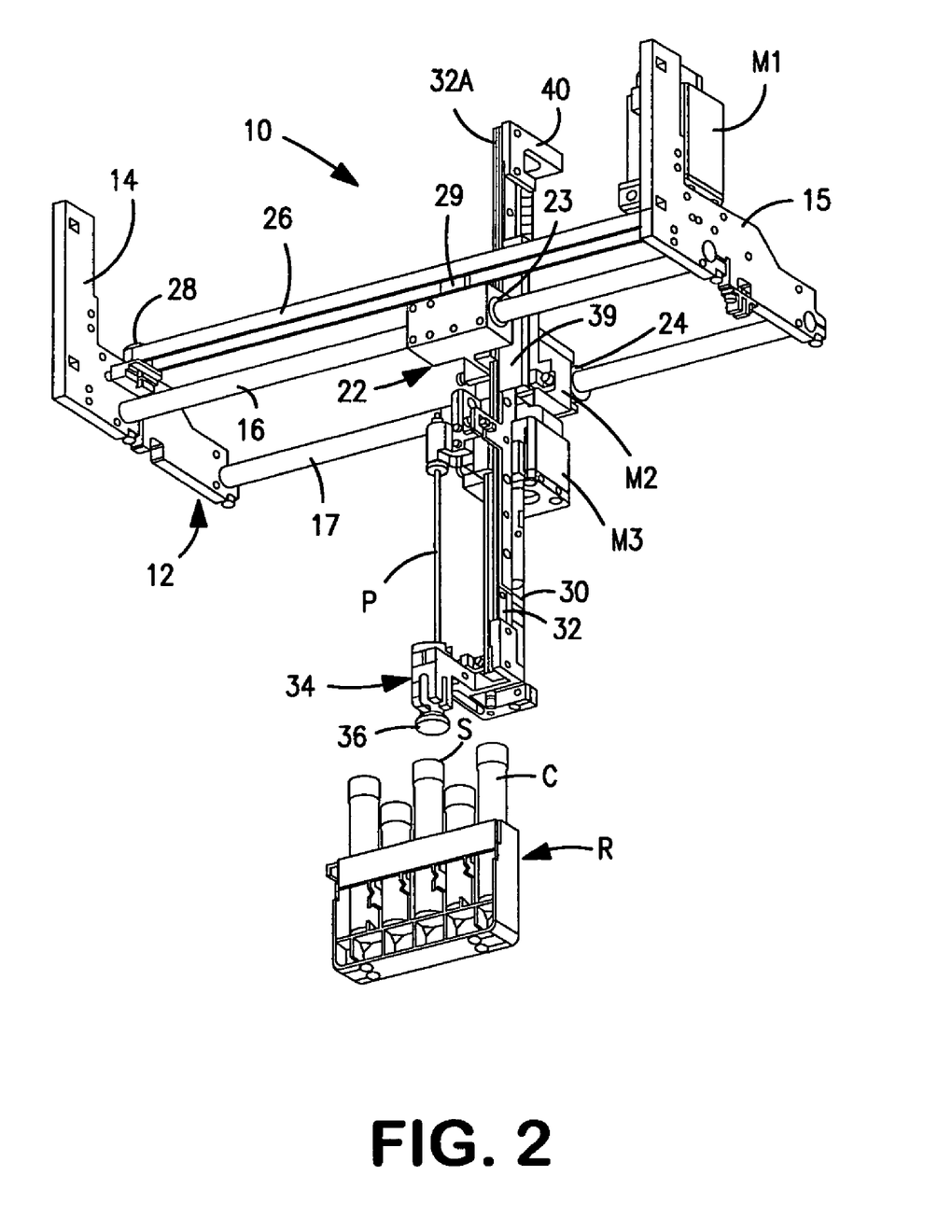
Figure 3:
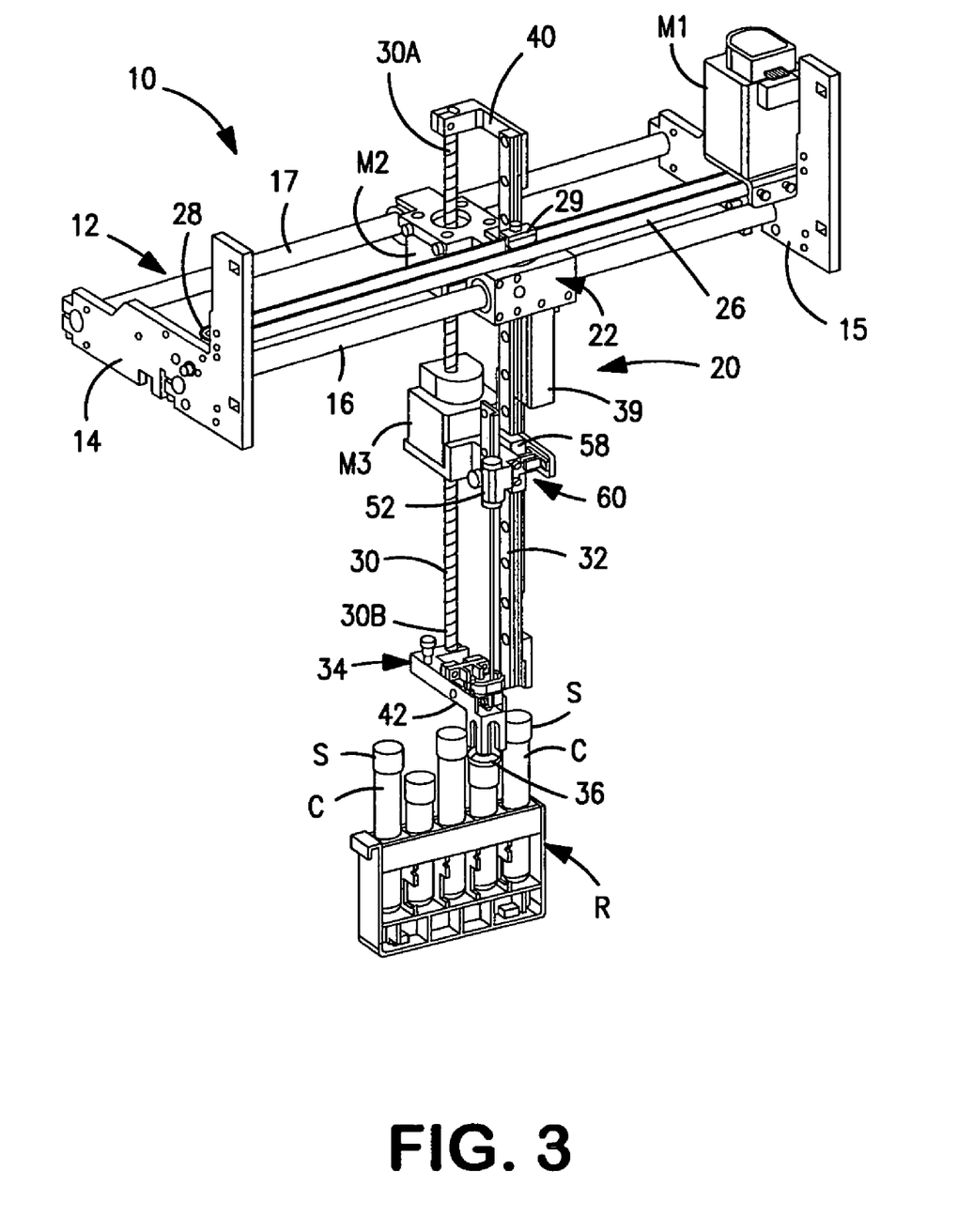
Figure 8:
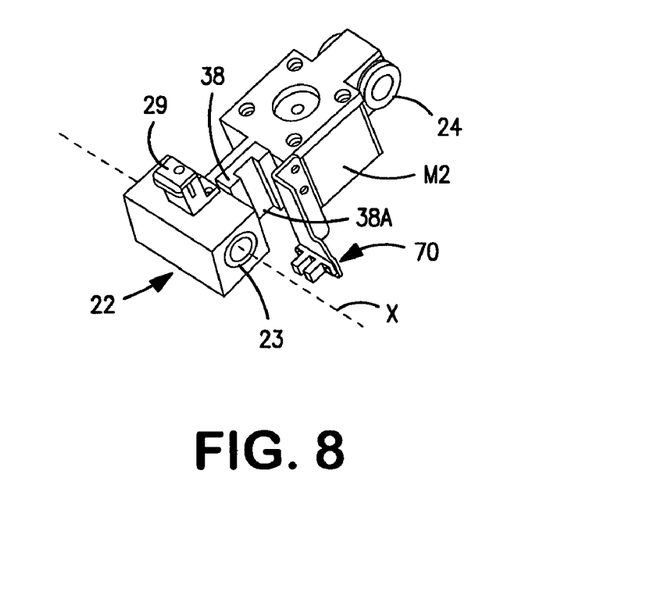
FIG. 8 is a perspective view of the X-Truck assembly of the FIG. 1 apparatus.

The probe-support assembly 20 generally operates to selectively advance the aspiration probe P along the (vertical) Z-axis, towards and away from the top surface of an underlying tube stopper S. As best shown in FIGS. 2 and 3, assembly 20 comprises (i) a pair of drive motors M2 and M3, (ii) a vertically-oriented linear drive member 30, which preferably takes the form of a precision lead screw (as shown) or a linear rack, (iii) a slidably-mounted and vertically-oriented guide rail 32, and (iv) a tube detector/stripper assembly 34. As best shown in FIG. 8, the lead screw 30 and guide rail 32 are rigidly connected to each other at their respective ends by a bracket 40 and by a housing 42 comprising the tube-detector/stripper assembly 34; thus, it will be appreciated that the lead screw 30 is not free to rotate.

Each of the drive motors M2 and M3 preferably comprises a conventional stepper motor that receives control signals from a suitably programmed microprocessor that directs the activity of the aspiration apparatus. Drive motor M2, referred to herein as the "stripper motor," is an integral part of the housing of truck 22; thus, the stripper motor is slidably-supported on the frame 12 for movement along rails 16 and 17, i.e., along the X-axis. As best shown in FIG. 2, the weight of motor M2 is supported primarily by rail 17. When drive member 30 comprises a conventional lead screw, motor M2 contains a rotatably-mounted nut having an internal thread that drivingly-engages the spirally wound thread of the lead screw. In response to an energizing current, motor M2 operates to incrementally rotate such nut, thereby advancing the lead screw axially, with respect to the motor housing, along the Z-axis.

Figure 9:
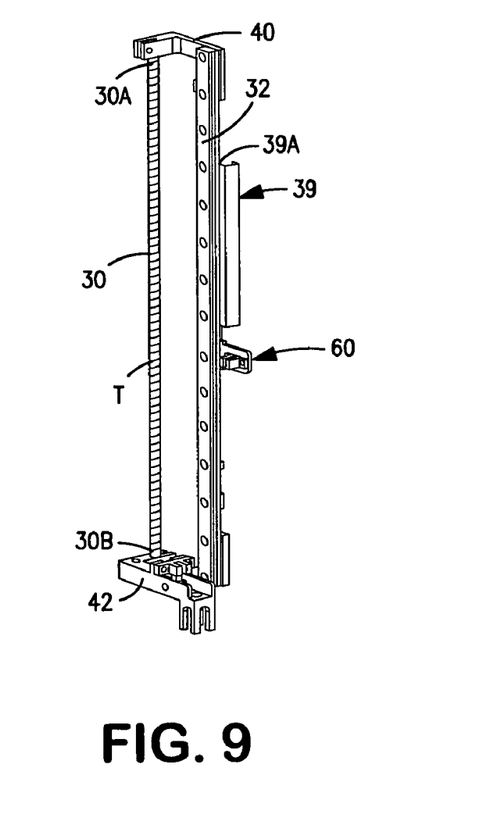
FIG. 9 is a perspective view of the lead screw/rail assembly of the FIG. 1 apparatus.

As noted above, the lower end 30B of the lead screw is attached to the tube detector/stripper assembly 34. Thus, as the lead screw moves axially downward from its "home" position (shown in FIGS. 1 and 2) to the downwardly-extended position (shown in FIGS. 3 and 4), assembly 34 moves from a position in which it is spaced from an underlying stoppered tube, to a position in which its inverted cup-shaped tube-positioning member 36 is located in pressing contact with the top surface of a tube stopper S. Vertical movement of the lead screw is guided by the above-mentioned linear guide rail 32 which is slidably-mounted for precise vertical movement in a track 38 carried by the truck 22 (see FIG. 8). The guide rail 32 is slidably-mounted within track 38. One end 39A of a U-shaped channel member 39 (best shown in FIG. 9) connected to rail 38 acts as a sensor flag, which interacts with sensor 70 carried by truck 22 to sense the upper and lower traveling limits of the guide rail 32. Since the lead screw and guide rail are interconnected at their respective ends, energization of the stripper motor M2 causes the entire lead screw/guide rail assembly (shown in FIG. 9) to move vertically, precisely along the Z-axis, as guided by track 38.

Figure 1:
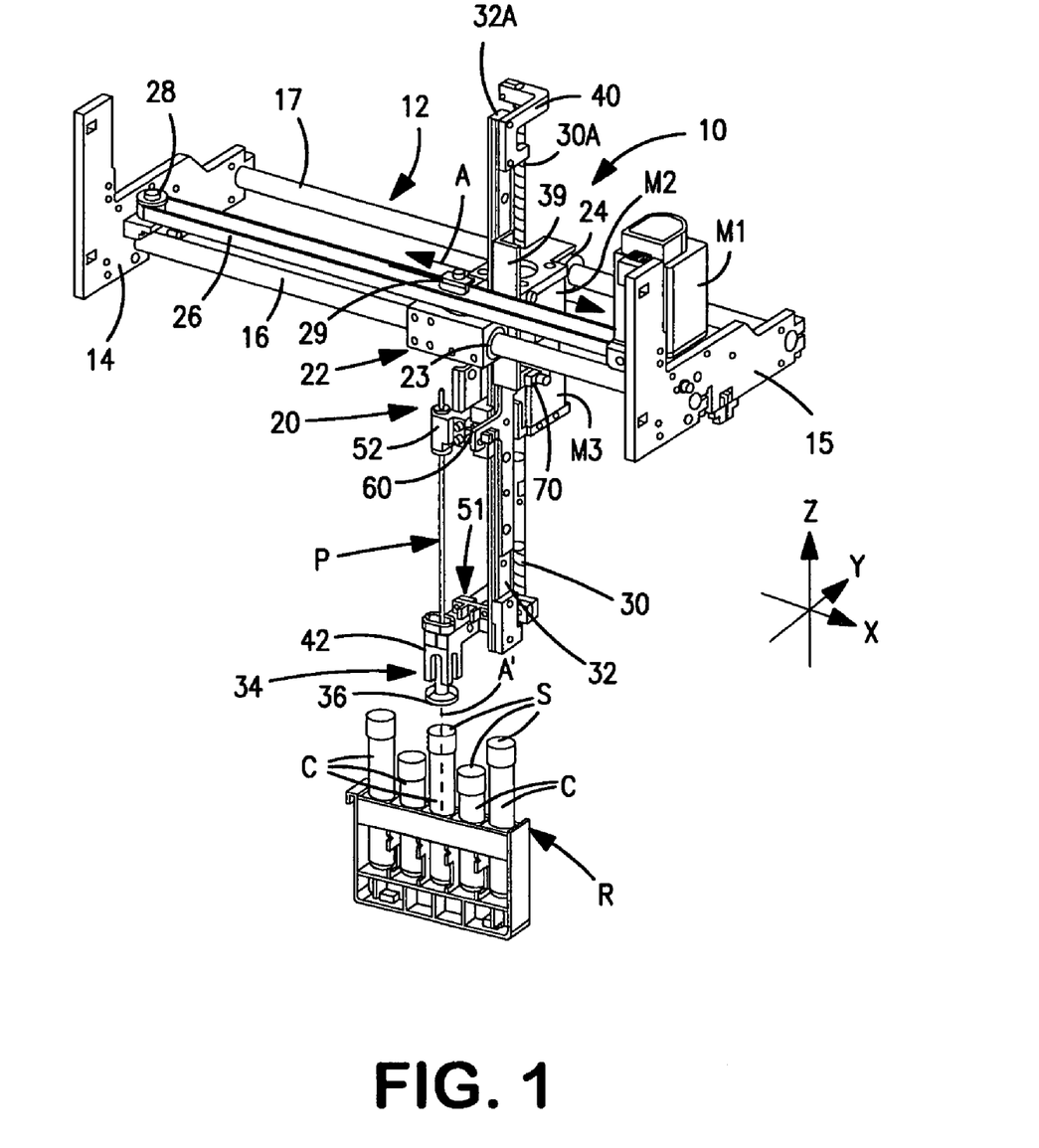
FIGS. 1-4 are perspective illustrations of a preferred embodiment of the apparatus of the invention, showing its various components in different operating positions.
Figure 6:
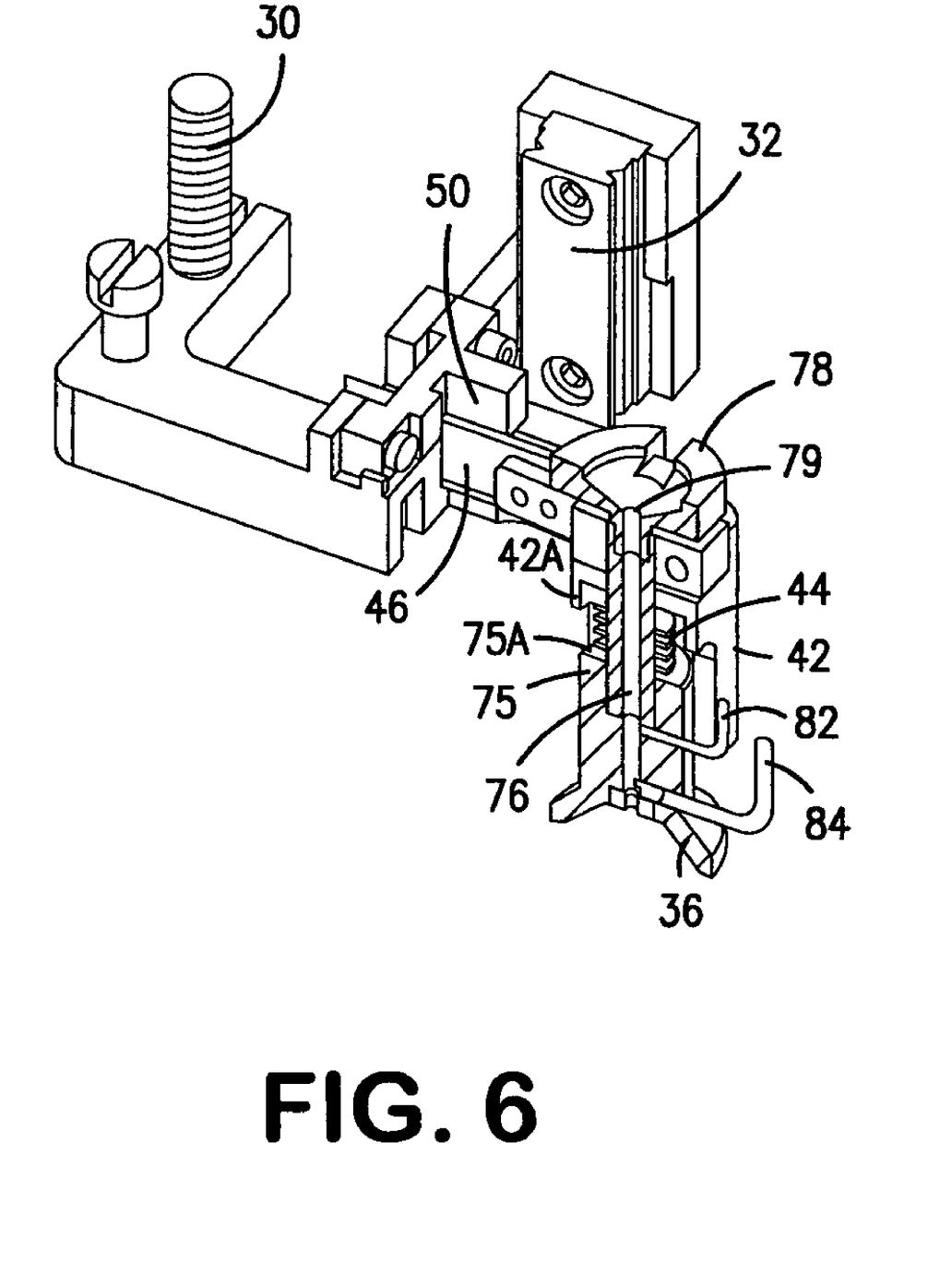
FIG. 6 is a perspective illustration of the FIG. 5 apparatus with a portion being in cross-section to reveal the structural details of the probe-washing component.
Figure 7A:
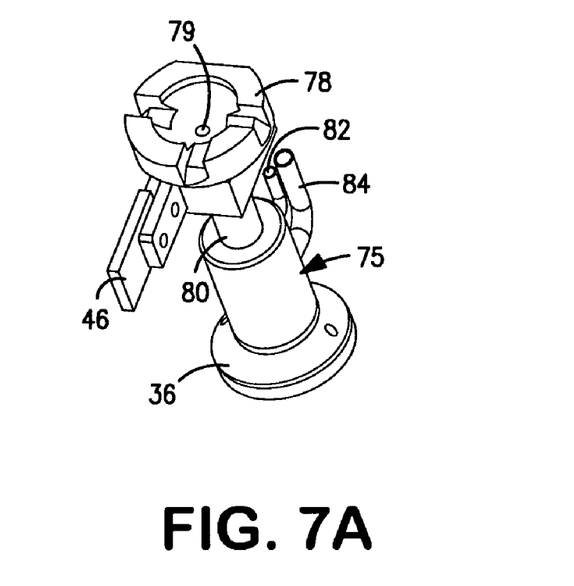
FIGS. 7A and 7B are perspective views of a preferred tube-detector/stripper member of the type used in the FIGS. 5 and 6 apparatus.
Figure 7B:
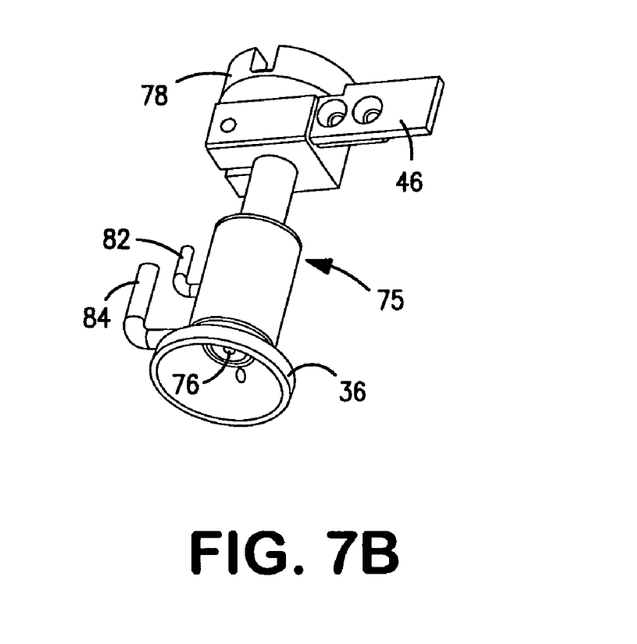

As drive motor M2 operates to drive the lead screw 30 downward from its home position shown in FIG. 1, the tube-positioner 36 of the tube detection/stripper assembly 34 eventually contacts and presses down upon an underlying stopper on a liquid container C. It will be appreciated that the tube rack R comprises a plurality of tube compartments, each containing a pair of opposing spring-loaded members which act on opposite sides of a tube within a compartment to align the tube axis with the central axis of each compartment and with a nominal axis. Owing to slight differences in spring constants, manufacturing tolerances, etc., the actual axis of each tube may be slightly offset from the nominal axis. Owing to its concave shape, member 36 will operate to slightly adjust the lateral position of underlying tube stopper as member moves downward. Such adjustment will cause the center of the stopper to be brought into alignment with the aspiration probe which passes through an aperture formed in the center of member 36. The continued operation of stripper motor M2 after the tube-positioning member 36 engages a tube stopper will cause member 36, and the stripper member housing 75 (shown in FIG. 6) of which it is an integral part, to slide upwardly (e.g., by several millimeters) in its support housing 42 and against the restoring force of an internal compression spring 44, also shown in FIG. 6. As member 36 moves upwardly, a flag 46, rigidly connected to such member and made of a ferromagnetic material, will move between the opposing magnetic pole pieces 48, 50 of a magnetic sensor 51 mounted atop housing 42, thus initiating a control signal to stop the driving current applied to motor M2. However, a holding current will continue to be applied to the motor M2 to maintain the vertical position of the lead screw and to maintain pressure on the tube stopper throughout the aspiration and stopper-stripping steps to follow.

After the control signal is produced by the afore-mentioned magnetic sensor 51, thereby indicating that a tube is in position for liquid aspiration, an energizing current is applied to the drive motor M3, referred to herein as the "piercing probe motor." As noted above, the piercing probe motor M3 may be substantially identical to that of stripper motor M2; preferably, however, motor M3 further includes an encoder to precisely control the vertical position of the probe tip. As best shown in FIG. 3, the piercing probe motor M3 is totally supported by the lead screw 30 passing through it; however, motor M3 is mechanically connected to the linear guide rail 32 via a slider member 58 that is mounted for sliding movement along the guide rail. Thus, in response to an energizing current being applied thereto, motor M3 will move axially along the axis of the lead screw 30 in a direction determined by the polarity of the energizing current. As motor M3 moves downward along the lead screw and along a vertical path determined by the linear guide rail 32, the aspiration probe will be driven in a downward direction from its "home" position, shown in FIG. 3, to its liquid-aspiration, shown in FIG. 4, where the tip of the aspiration probe has punctured the tube stopper and is submerged in the liquid L to be aspirated. As best shown in these drawings, the probe holder 52, which engages and supports the top end of the aspiration probe, is rigidly mounted on slider member 58; thus, as the slider member moves vertically along rail 32 under the force applied by motor M3, the probe moves accordingly.

Figure 4:
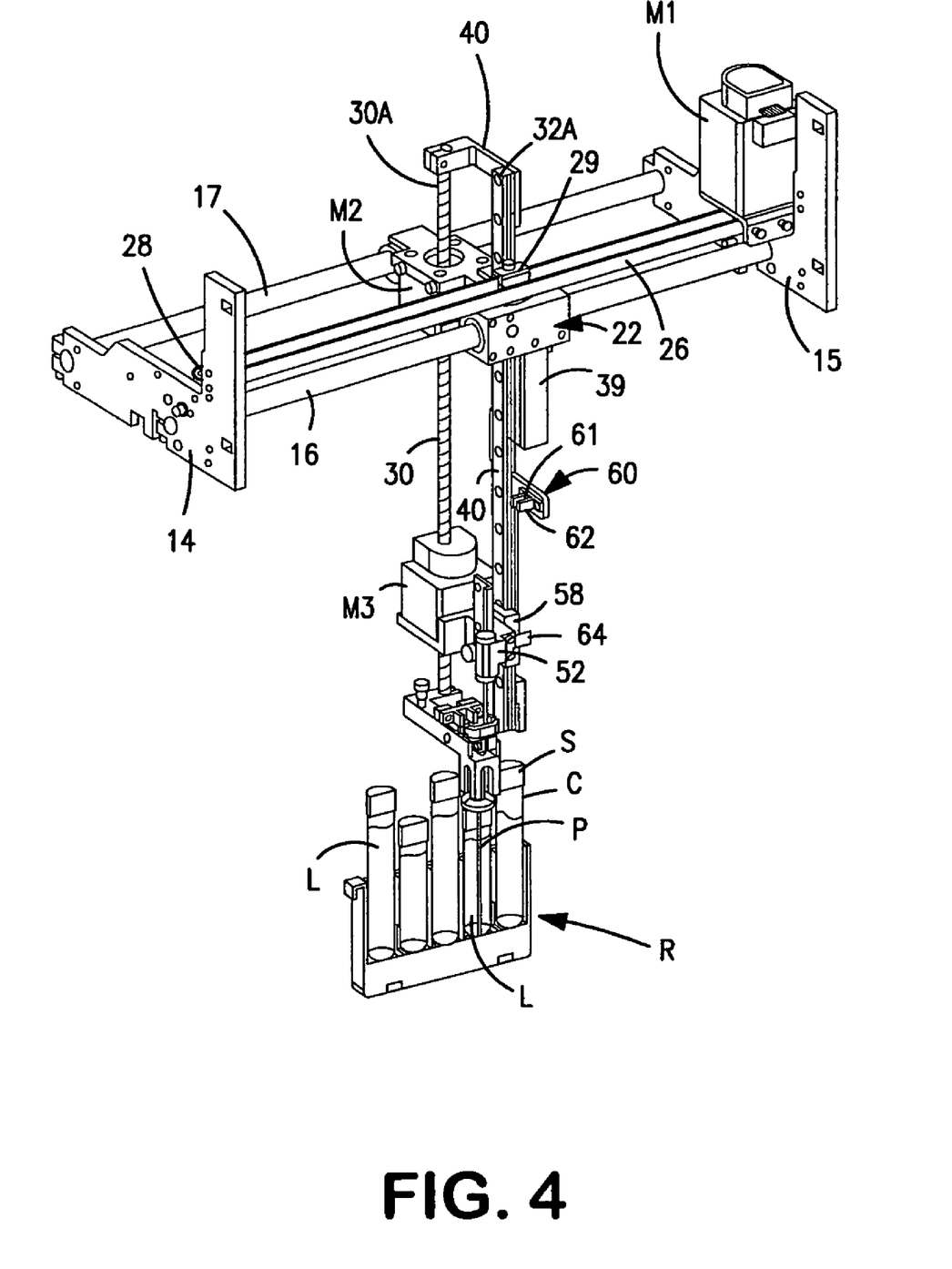
Figure 5:
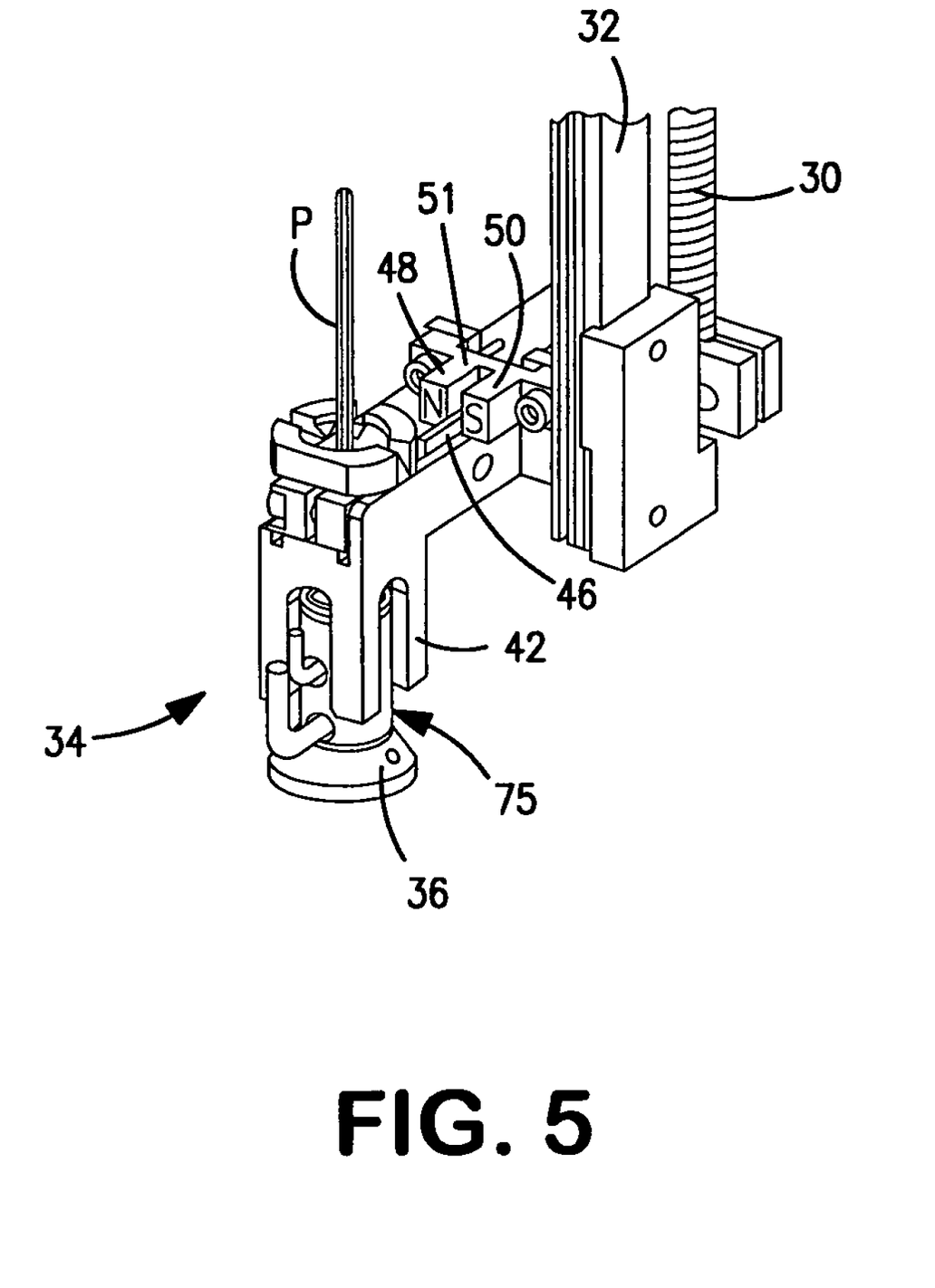
FIG. 5 is an enlarged perspective view of the tube detector/stripping member of the apparatus shown in FIGS. 1-4.

As best shown in FIG. 4, the probe's home position is detected by a second magnetic sensor 60 comprising a spaced pair of magnetic pole pieces 61 and 62 of opposite polarity mounted on a flange extending from guide rail 32. A flag 64 of ferromagnetic material carried by the probe holder 52 produces a detectable change in the magnetic flux between the pole pieces when the probe is in its home position. The home position of the piercing probe motor M3 is detected by a third magnetic sensor 70 mounted on the truck 22 (see FIG. 8). Sensor 70 detects a flag (not shown) carried by the housing of motor M3. Obviously, a suitable photoelectric sensor could be substituted for any or all of the magnetic sensors 51, 60 and 70. As will be appreciated, the requisite tubing by which the liquid aspirated by the probe is transmitted to a metering or processing station is not shown for the sake of clarity. The distal end of the probe is initially shielded in a probe-washing station which, as explained below, is preferably a part of assembly 34.

After the aspiration probe has penetrated a tube stopper and aspirated liquid from an associated tube, the piercing probe motor M3 is operated in a reverse direction to raise the mechanically-linked probe and to return it to its home position. During this time and throughout the liquid-aspirating process, the holding current applied to the stripper motor maintains the spring-biased engagement between the tube-positioning member 36 and the tube stopper. This engagement prevents the tube stopper from following, due to frictional forces, the movement of the probe as the latter is withdrawn from the tube and, in effect, strips the stopper from the probe.

Referring to now FIGS. 5, 6, 7A and 7B, the tube-detector/stripper assembly 34 is shown as comprising the above-noted inverted cup-shaped tube-positioning member detector 36. The latter is an integral part of a stripper member housing 75 that is slidably-mounted within the stripper assembly housing 42. The cup-shaped member 36 is designed to center a tube precisely on the probe axis as member 36 descends upon a tube stopper and, in doing so, detect the presence of a tube for liquid aspiration. The stripper member housing has a central channel 76 that normally surrounds the distal portion of the probe, including the probe tip, when the probe is not being used to aspirate liquid. Housing 75 also comprises an integral concave circular tray 78 at its top that serves to collect drops or film of aspirated liquid that may cling to the probe surface after aspiration. Tray 78 has a central opening 79 through which the probe enters channel 76. The afore-noted compression spring 44 surrounds a central stem portion 80 of housing 75 and is supported between a shoulder 75 on housing 75 and an inside wall 42A of housing 42. Preferably, the stripper housing further defines a probe washing station comprising an input port 82 through which a washing liquid can be introduced into the probe channel 76 from an external pressurized source, and a waste port 84 through which the washing liquid is collected during the washing process.

While the invention has been described with reference to a preferred embodiment, it will be appreciated that various changes can be made without departing from the spirit of the invention. For example, the apparatus described can be used to access liquid from an open container or tube. In such case, the "stripping" action by which the probe is stripped from a stoppered container is not necessary. However, the tube-detecting and centering function of assembly 34 is still provided as the cup-shaped member engages the open end of the tube during its downward travel. Such changes are intended to fall within the scope of the appended claims.

What is claimed is:

1. Apparatus for aspirating a volume of liquid contained in a sealed tube having a puncturable stopper mounted at one end thereof, said apparatus comprising
   (a) a frame;
   (b) a linear guide rail slidably supported by said frame;
   (c) a liner drive member mounted on said linear guide rail;
   (d) a first drive motor supported by said frame and being adapted, in response to having a first electrical current applied thereto, to selectively and incrementally advance said linear drive member in either of opposite directions along a predetermined path leading towards or away from said puncturable stopper on said tube, said path being substantially parallel to the central longitudinal axis of said tube;
   (e) a tube detector/stripper member mounted at one end of said linear drive member, said tube detector/stripper member being adapted to engage the top of said puncturable stopper as said linear drive member is advanced along said predetermined path towards said puncturable stopper, Whereby said tube detector/stripper member detects, upon contacting said puncturable stopper, that a tube is in a position to have liquid aspirated therefrom;
   (f) a second drive motor supported by said linear drive member and being adapted, in response to having a second electrical current applied thereto, to incrementally advance in either of opposite directions along a axis of said linear drive member, towards and away from said puncturable stopper; and
   (g) an aspiration probe rigidly connected to said second drive motor, said aspiration probe being aligned with the central longitudinal axis of said tube when said tube detector/stripper member is in contact with a puncturable stopper, said probe having a sharp tip adapted to puncture said puncturable stopper and thereby enter the interior of said tube as said second drive motor moves along the axis of said linear drive member towards said puncturable stopper.

2. The apparatus as defined by claim 1 wherein said linear drive member comprises a lead screw having a threaded outer surface, and wherein each of said first and second drive motors comprises an electric motor that is adapted to drivingly engage said threaded outer surface to produce relative motion between said drive motor and said lead screw.

3. The apparatus as defined by claim 2 wherein said linear guide rail is provided to guide said aspiration probe along said central longitudinal tube axis as said second drive motor is advanced along said linear drive member, said linear guide rail being rigidly connected to said second drive motor, whereby said linear guide rail moves in a direction substantially parallel to said linear drive member as said linear drive member is advanced along said predetermined path by said first drive motor.

4. The apparatus as defined by claim 1 wherein said linear drive member comprises a linear rack of gear teeth, and wherein said first and second drive motors comprises electric motors having rotatably-mounted pinions that engage said rack.

5. The apparatus as defined by claim 1 wherein said tube-detector/stripper member comprises an inverted cup-shaped member by which said a tube can be centered along the axis of the aspiration probe.

6. The apparatus as defined by claim 1 wherein said tube-detector/stripper member comprises a housing defining a probe-washing chamber in which said probe tip can be washed after each liquid aspiration.

7. Apparatus for aspirating a volume of liquid contained in a sealed tube having a puncturable stopper mounted at one end thereof, said apparatus comprising
   (a) a frame;
   (b) a linear guide rail slidably mounted on said frame;
   (c) a linear lead screw operatively coupled to said linear guide rail; wherein said guide rail guides the movement of said linear lead screw along said predetermined path and to move along a path parallel to said predetermined path;
   (d) a first drive motor supported by said frame and adapted, in response to having a first electrical current applied thereto, to selectively and incrementally advance said linear lead screw along a predetermined path generally towards or away from said puncturable stopper on said tube, said predetermined path being substantially parallel to the central longitudinal axis of said tube;
   (e) a tube detector/stripper member mounted on a housing connecting said linear guide rail with said lead screw, said tube detector/stripper member being adapted to engage the top of a puncturable stopper mounted at one end of a tube as said linear drive member is advanced along said predetermined path towards said puncturable stopper, whereby said tube detector/stripper member detects that a tube is in a position to have liquid aspirated therefrom;
   (f) a second drive motor supported by said linear lead screw and being adapted, in response to having a second current applied thereto, to selectively and incrementally move in either of opposite directions along a surface of said linear lead screw, towards or away from said puncturable stopper; and
   (g) an aspiration probe rigidly connected with said second drive motor, said aspiration probe being aligned with said central longitudinal axis of said tube when said tube detector/stripper member is in contact with a puncturable stopper, said aspiration probe being adapted to puncture said puncturable stopper and thereby move to a liquid-aspiration position within the interior of said tube as said second drive motor moves along the surface of said linear lead screw towards said puncturable stopper.

8. The apparatus as defined by claim 7 wherein said tube detector/stripper member is maintained in engagement with said puncturable stopper while said aspiration probe is withdrawn from said liquid aspiration position to a position outside said sealed tube by applying a holding current to said first drive motor during such withdrawal movement of said probe, whereby said aspiration probe is stripped from the puncturable stopper without causing substantial movement of the sealed container.

9. The apparatus as defined by claim 7 wherein said tube detector/stripper member comprises a housing defining a probe-washing chamber in which said probe can be washed after each liquid aspiration.

\* \* \* \* \*